United States Patent [19]

Allen et al.

[11] Patent Number: 4,746,551

[45] Date of Patent: May 24, 1988

[54] REHYDRATABLE POLYACRYLAMIDE GELS

[75] Inventors: Robert C. Allen, Isle of Palms, S.C.; Bertold J. Radola, Munich, Fed. Rep. of Germany

[73] Assignee: Micro-Map, Inc., Boca Raton, Fla.

[21] Appl. No.: 643,727

[22] Filed: Aug. 24, 1984

[51] Int. Cl.$^4$ .............................................. B05D 3/02
[52] U.S. Cl. ............................... 427/389.7; 427/385.5; 427/393.5; 427/407.2; 427/412.5
[58] Field of Search ............... 427/393.5, 385.5, 389.7, 427/407.2, 412.5

[56] References Cited

U.S. PATENT DOCUMENTS

| | | | |
|---|---|---|---|
| 3,875,044 | 4/1975 | Renn et al. | 204/182.8 |
| 4,006,069 | 2/1977 | Hiratsuka et al. | 204/182.8 |
| 4,189,370 | 2/1980 | Boschetti | 204/182.8 |

OTHER PUBLICATIONS

Ruchel, et al., *Anal. Biochem.*, 68:415 (1975).

*Primary Examiner*—Edward J. Smith
*Assistant Examiner*—J. M. Reddick
*Attorney, Agent, or Firm*—Bernard, Rothwell & Brown

[57] ABSTRACT

The present invention relates to rehydratable polyacrylamide gels. The rehydratable gels can be stored at room temperature for long periods of time and rehydrated with various materials to provide a suitable matrix for various electrophoretic separations.

10 Claims, 1 Drawing Sheet

REHYDRATABLE POLYACRYLAMIDE GELS

TECHNICAL FIELD

The present invention relates to a process for the preparation of rehydratable, multipurpose polyacrylamide gels, which can be stored for extended periods at room temperature.

BACKGROUND OF THE INVENTION

Polyacrylamide gels are used as a gel support matrix for various electrophoretic processes, including separation procedures such as isoelectric focusing, conventional continuous zone electrophoresis, or discontinuous zonal electrophoresis. Normally, polyacrylamide gels are prepared individually just prior to use, otherwise the gels must be stored in sealed containers at refrigerated temperatures and for only limited periods of time. The gels are generally prepared for a specific purpose with a specific buffer system. Efforts have been made in the past to increase their longevity by dehydrating the gels for storage, then rehydrating them for use. This approach, however, caused irreversible damage to the gel structure, such that subsequent separation of biological or other charged macromolecules by electrophoretic methods with the gel was unsuccessful. Therefore, there still exists a need for a polyacrylamide gel matrix that can be stored over long periods of time at room temperature for subsequent use in electrophoretic methods of separating macromolecules.

It therefore is an object of the present invention to provide a process for drying polyacrylamide gels for storage at room temperature followed by rehydration for the electrophoretic separation of macromolecules. It also is an object of the present invention to provide polyacrylamide gels which can be impregnated during rehydration with a variety of reagents for the visualization of components separated by the electrophoretic process.

It is a further object of the present invention to provide a support material for electrophoretic separation or biochemical reactions that is free from contaminants typically found in conventionally prepared polyacrylamide.

It also is an object of the present invention to provide rehydratable polyacrylamide gels that can be used as reagent carriers for the visualization of macromolecules separated by the electrophoretic process.

SUMMARY OF THE INVENTION

The present invention provides a process for the preparation of a rehydratable polyacrylamide gel comprising
(a) polymerizing acrylamide monomers to form a gel;
(b) removing from the gel any residual components of the polymerization;
(c) adding to the gel a stabilizing amount of at least one polyol, polymeric alcohol, polysaccharide or polyamine; and
(d) thereafter drying the gel.

The present invention also relates to a rehydratable polyacrylamide gel comprising a dehydrated cross-linked polyacrylamide gel containing a stabilizing amount of at least one polyol, polymeric alcohol, polysaccharide or polyamine.

DETAILED DESCRIPTION OF THE PREFERRED EMBODIMENT

Figure 1:
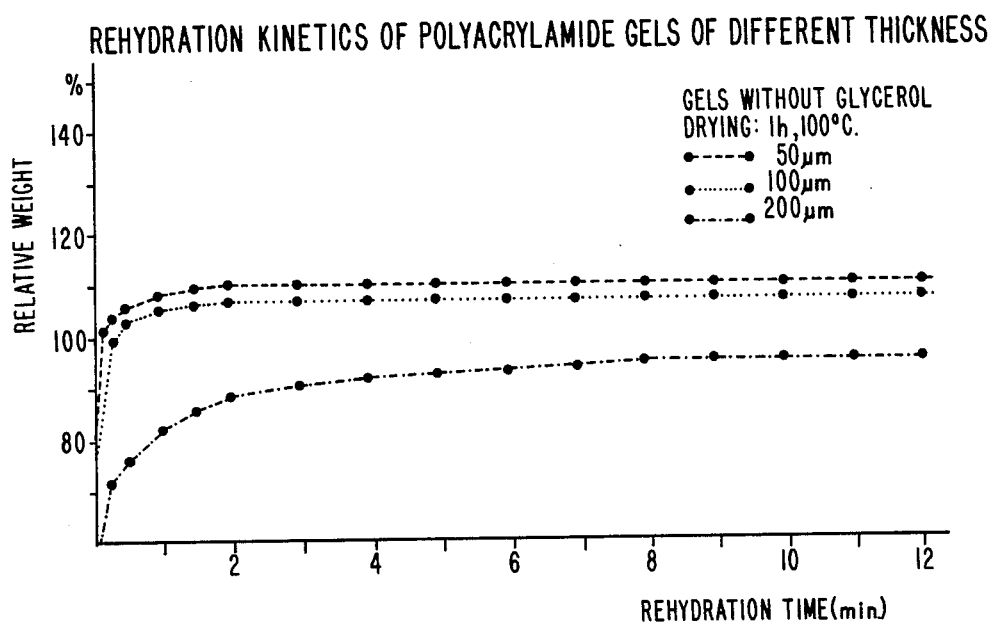
FIG. 1 shows the rehydration kinetics of a polyacrylamide gel prepared without a stabilizing agent incorporated into the gel during the washing process before drying.

In accordance with the present invention there is disclosed a method for making storage stable, rehydratable polyacrylamide gels useful in the electrophoretic separation of macromolecules and in the visualization process of various biological materials. It has been discovered that polyacrylamide gels can be dehydrated for storage purposes and then rehydrated for use without suffering irreversible loss of functionality by adding a stabilizing amount of one or more polyols, polymeric alcohols, polysaccharides or polyamines to the gel before it is fully dried. If desired, the gels can be impregnated with reagents during rehydration to aid in the visualization process of various components separated by the electrophoretic processes.

The polyacrylamide gels useful in accordance with this invention are made from acrylamide monomers which are polymerized in the presence of crosslinkers in accordance with conventional methods known to those skilled in the art. It is desirable to use purified acrylamide monomers to form the polyacrylamide gels; impurities in the material can interfere with the polymerization reaction.

The acrylamide can be readily polymerized in aqueous solutions at elevated temperatures with free radical initators such as t-butyl hydroperoxide, hydrogen peroxide, the alkali metal and ammonium persulfates, chlorates, perborates, percarbonates, and the like. Redox catalyst systems are frequently employed for polymerization at low temperatures, particularly where high-molecular-weight polymers are desired. Redox systems consist of oxidizing agents, such as the initiators cited above, and together with reducing agents, such as thiosulfates or bisulfites. The polymerization of the monomers also may be accomplished by photopolymerization in the presence of riboflavin, or other photoactive polymerizing agents, or it may be carried out in the absence of a chemical polymerizing agent by irradiation, such as with high energy electron beams.

The unpolymerized starting reagents can be applied to a mold in accordance with conventional methods, including rolling on or sliding in closed systems, or in open systems under reduced oxygen tension. With an excess of three radical producing components to accelerate polymerization, polymerization in atmospheric oxygen may also be used.

Although the monomer may be polymerized in a variety of polymerization vessels, preferably the reagents are poured onto a support material which will bond to the polymerized gel. Examples of such support materials include treated hydrophilic polyester sheets, mylar films or glass plates which have been rendered hydrophilic by treatment with agents such as silanes. Suitable supports are commercially available and include Gelfix, which is manufactured by Serva Fein Biochemicals of Heidelberg, Germany and GelBond-PAG manufactured by Marine Colloids of Rockland, Maine. By carrying out the polymerization on glass supports, the polyacrylamide gel is covalently linked to the glass plate.

One advantage in using a polyacrylamide as a separation media is that one can effectively control the pore size of the gel. The effective pore size of a polyacrylamide gel is an inverse function of "total monomer concentration", which is defined as the sum of the concentrations of acrylamide monomer and the crosslinking agent. A polyacrylamide gel of low concentration appears to be a pore-meshed, three dimensioned lattice of long polyacrylamide chains which are connected at distant intervals by the crosslinker. When the percent of acrylamide monomer is increased and a low percent of crosslinker is maintained, the frequency of polymeric chains increases, thereby reducing the pore size. This has been shown for gel concentrations of up to 40 and even 50% of acrylamide monomer and at 5% of crosslinking agent. As cross-linking is increased, a regular array of chains, linked by the crosslinker is formed which, at 5 percent crosslinker has maximum sieving properties, i.e. minimum pore size with a constant value of acrylamide monomer. The total monomer concentration can be from about 4.5% to about 50% and preferably 6.0% to about 10%. The concentration of the acrylamide monomer can be from about 2.5% to 30%, with 3% to 12% being preferred. The concentration of the crosslinker monomer is generally from about 2% to 20%, with 3% to 5% being preferred.

The cross-linking agents for use in the preparation of the polyacrylamide gels of the present invention include conventional cross-linkers including methylenebisacrylamide, $N,N_1$-diallyltartardiamide, polyolefinic agarose, $N,N_1$-(1,2-dihydroxyethylene) bisacrylamide, ethylene diacrylate, polyethylene glycol diacrylate, and N, N'-bisacrylcystamine or mixtures thereof. Preferably methylenebisacrylamide or polyolefinic agarose are used.

After the monomers have been polymerized, the residual components of the polymerization reaction are removed. While any efficient method of removal can be used, one method which has been found successful is to wash the gels in distilled water for a period of time sufficient to remove any residual components of the polymerization process, such as unpolymerized monomers, catalysts and other unreacted components. By removing the residual components, the final product shows a reduction in conductance of up to seven-fold over similar gels prepared conventionally. This property allows higher initial voltage gradients with reduced Joule heat, thereby shortening the separation time with the potential of improving resolution in isolectric focusing as well as in conventional electrophoresis.

Following the removal of the residual components, a stabilizing amount of one or more polyols, polymeric alcohols, polysaccharides or polyamines is added to the gel. The stabilizers can be added by equilibration in a solution containing the polyol, polymeric alcohol, polysaccharide or polyamine. The gel can also be partially dried and rehydrated with the polyol, polymeric alcohol, polysaccharide or polyamine followed by partial drying of the gel. Examples of suitable polyol compounds include glycerol and glycols having from about 2 to about 700 carbon atoms. Preferably the glycols have from about 2 to about 20 carbon atoms. A polymeric alcohol also can be used. Polymeric alcohols of either synthetic or biological origins may be used in the preparation of the present invention. Examples of such polymeric alcohols include polyethylene glycol, and polyvinyl alcohol. Various polysaccharides, such as dextran, and polyamines, such as polylysine, also can be used. A preferred stabilizer is dextran (75,000 molecular weight). It has been found that the addition of a polyol, polymeric alcohol, polysaccharide or polyamine controls the residual wetness of the gels and/or interacts with the polymer, thereby protecting the gel from irreversible damage on prolonged storage. The polyol, polymeric alcohol, polysaccharide or polyamine may be added alone or in combination in amounts of from about 5 to about 30% by volume to the total volume of the polyacrylamide gel. Preferably, about 7 to about 10% by volume is added.

After the polyol, polymeric alcohol, or polysaccharide or polyamine has been added to the polyacrylamide gel, the gel is dried. Various methods of drying may be employed, including air drying at room temperature or drying with infrared lamps, fans or in ovens at elevated temperatures, i.e. 45–120° C., for accelerated drying.

The polyacrylamide gels of the present invention can be in a variety of forms including sheets, films, cylinders, columns, etc. When the gels are in the form of sheets, they can be of conventional thicknesses, such as from about 30 microns to about 500 microns. Preferably the gel sheets are of a thickness of from 50 to 300 microns.

The dried gels containing a polyol stabilizer, such as glycerol, can be overlaid with plastic or a metallic repellent film, such as polyvinyl chloride, polypropylene, or triacetate. Dried gels stabilized with polymeric alcohols or a polysaccharide, e.g. dextran, may be stored in a variety of containers such as envelopes, boxes, etc. since their surface is essentially glass-like.

Figure 2:
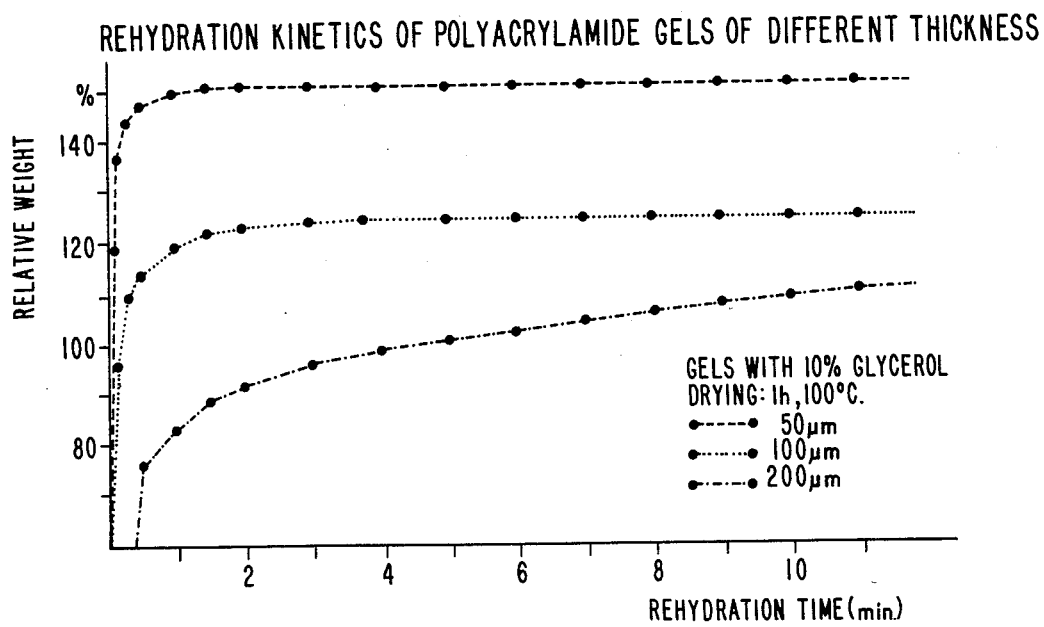
FIG. 2 shows the rehydration kinetics of a polyacrylamide gel with 10% (v/v) glycerol incorporated into the gel.

The dehydrated polyacrylamide gel may be rehydrated with various solutions depending upon the intended use of the gel. Various methods can be used to rehydrate the gels. One method is to roll the gel onto a plate containing the proper volume of solution or reagent. The gels also may be rehydrated by any means of saturation such as spraying, immersing or floating the gel in the desired solution. The rehydration kinetics of the polyacrylamide gels of the present invention are superior to those gels without the stabilizer(s). FIGS. 1 and 2 demonstrate that for the same gel thickness, the percentage of absorption of the present invention is substantially higher than those gels without the glycerol.

Due to the absorbent properties of polyacrylamide upon rehydration, the polymeric matrix swells, automatically opening the pore size of the gels and providing a less restrictive matrix which allows the migration of larger macromolecules. By adjusting and controlling the amount and type of solution which is absorbed, one can control directly the particular size of macromolecules which will be retained or passed through the polyacrylamide gel. This advantage allows the use of the sieving effect in continuous or discontinuous buffer systems to separate the macromolecules on the basis of size and charge rather than by charge alone, as in isoelectric focusing. Thus, large molecules, i.e. greater than 200,000 daltons, will be less restricted and will reach their isoelectric points in a shorter time under similar conditions of voltage and milliamperage.

The polyacrylamide gel of the present invention provides a multipurpose support matrix material. This matrix material can be used for electrophoretic processes in a wide variety of separation procedures, such as isoelectric focusing, conventional continuous zone electrophoresis, or discontinuous zonal electrophoresis, by rehydrating the media with a defined volume of the appropriate buffer or ampholyte. Isoelectric focusing separations can be enhanced through the use of polyacrylamide gels of the present invention.

The process of the present invention produces acrylamide gels which can be used as reagent carriers for rapid enzyme visualization with a minimal amount of diffusion. This can be achieved by controlling the reaction product volume and reaction time at elevated temperatures and precisely controlling the quantification with appropriate control of monomer concentration and the volume during rehydration of the same basic gel matrix. The gel matrix can be rehydrated with various substrates and dye complexes and/or helper enzymes and thereafter applied to the surface of the gel on which the electrophoretic separation is carried out. The appropriate reaction then can be carried out at conventional times and temperatures under controlled volumes and in an environment limiting diffusion which would otherwise decrease resolution.

In a further embodiment of this invention, monoclonal or polyvalent antibodies may be impregnated into the gel of the present invention. By impregnating such antibodies, one may obtain specific antibody-antigen reactions in both the separating and overlaid gel which may be demonstrated with appropriate stain procedures.

The polyacrylamide gel of the present invention may be impregnated by rehydrating the gel with other chemical and biological reagents, which may be heat labile. The impregnated gel can then be used in a variety of electrophoretic processes.

The polyacrylamide gel can be impregnated with additional reagents, such as glycerol, to adjust the surface proportion of the gel so that spreading of liquid samples may be avoided. This allows a direct sample application rather than the common paper tab method.

Other materials which may be impregnated on the dried gel or series of gels through rehydration include detergents, dissociating agents, or mixtures thereof. Examples of various detergents include conventional zwitter ionic detergents and sodium dodecylsulfate. One example of a dissociating agent is purified urea. Incorporation of these various reagents will allow one to perform specialized electrophoretic separations. For example, the gels allow the separation of dissociated macromolecules in the presence of urea by isolectric focusing in one dimension followed by separation in the presence or absence of the detergent or denaturing agent in the second dimension to obtain the higher detection of two-dimensional electrophoresis.

The polyacrylamide gels of the present invention allow any of the common electrophoretic separation methods to be performed from a single material. For example, isoelectric focusing gradients of any pH range, or with ampholytes of any manufacture, may be prepared simply by rehydrating the gel in the appropriate volume of ampholyte, where the same volumes required provide a substantial saving in reagent costs.

The following examples are supplied to illustrate, but not necessarily to limit, the present invention.

EXAMPLE 1

Recrystallization of Acrylamide

Into a suitable container, 45 grams of acrylamide are added to 90 ml. of chloroform heated to 60° C. in a hot water bath. After the acrylamide is dissolved at this temperature, the solution is filtered through Whatman #1 filter paper held in a funnel is placed in a heating jacket at 60° C. The filtrate is collected in a heating jacketed florence flask maintained at 60° C. After filtration, the wash containing the filtrate is cooled in an ice bath to no lower than 22° C. and immediately filtered under vacuum through Whatman #1 filter paper in a Buchner funnel until all the liquid is removed from the crystals. The monomer is then removed from the funnel and dried.

EXAMPLE 2

Preparation of Acrylamide Stock Solution

To a suitable reaction vessel there is added 2.88 grams of the recrystallized acrylamide prepared in Example 1, 100 mg of methylenebisacrylamide and 3.30 ml of distilled water. The solution then is heated to dissolve the monomer. This amount of 48% stock solution is sufficient for 40 ml of final gel volume.

EXAMPLE 3

Fifty $\mu l$ of N, N, N',N'-tetramethylenediamine (TEMED), 20 ml (55 mg/100 ml) of ammonium persulfate, and 15.30 ml (0.175M) of Tris-Cl are added to a glass beaker and mixed. This mixture is then combined with 4.62 ml of the acrylamide stock solution of Example 2 and immediately poured into the polymerization chamber. This is closed in such a manner that no air bubbles are entrapped. The chamber is kept closed for about 20 minutes to 1 hour at room temperature, until it is certain that the acrylamide has polymerized. The gel thereafter is removed from the chamber and washed several times in distilled water.

EXAMPLE 4

In a suitable shallow dish there is added a predetermined amount of glycerol (generally from 5% to 30% by volume of the total volume of the gel). The gel prepared in Example 3 is then immersed into the dish wherein it absorbs the glycerol. After the glycerol has been absorbed, the impregnated gel is then dried in a convection oven for 1 hour at 100° C. After the gel has been dried, the gel is overlaid with plastic, and packaged. Prior to using the gel, it is rehydrated, preferably in 10% (v/v) glycerol for approximately 20 minutes.

While certain representatie embodiments and details have been shown for the purpose of illustrating the invention, it will be apparent to those skilled in the art that various changes and modifications may be made therein without departing from the spirit or scope of the invention.

We claim:

1. A process for the production of a rehydratable polyacrylamide gel comprising:
    (a) polymerizing acrylamide monomers on a hydrophilic support material to form a gel, wherein the resulting polyacrylamide is covalently bonded to the support;
    (b) removing from the gel any residual components of the polymerization;
    (c) adding a stabilizing amount of a stabilizer which consists essentially of one or more polysaccharides; and
    (d) drying the gel.

2. The process of claim 1 wherein said polysaccharide is added in the form of a solution.

3. The process of claim 1 wherein said polysaccharide is added in a rehydration step following partial drying of the gel.

4. The process of claim 1 wherein said polysaccharide is dextran.

5. The process of claim 1 wherein polysaccharide is added in amounts of from about 5% to about 30% by volume of the total volume of the mixture.

6. The process of claim 7 wherein said polysaccharide is added in amounts of from about 7% to about 10% by volume of the total volume of the mixture.

7. The process of claim 1 wherein said support material is a hydrophilic polyester sheet or glass plate that has been treated with a silane compound.

8. The process of claim 1 wherein said polyacrylamide gel is in the form of a sheet.

9. The process of claim 8 wherein said sheet is from about 30 microns to 500 microns in thickness.

10. The process of claim 9 wherein said sheet is from about 50 microns to about 300 microns in thickness.

* * * * *